United States Patent
Dye et al.

(10) Patent No.: US 7,156,852 B2
(45) Date of Patent: Jan. 2, 2007

(54) METHOD OF USING T-HANDLE RULERS IN MINIMALLY INVASIVE HIP SURGERY

(75) Inventors: Donald Dye, Pflugerville, TX (US); John Krause, Austin, TX (US)

(73) Assignee: Zimmer Orthopedics, Inc., Austin, TX (US)

( * ) Notice: Subject to any disclaimer, the term of this patent is extended or adjusted under 35 U.S.C. 154(b) by 510 days.

(21) Appl. No.: 10/375,430

(22) Filed: Feb. 27, 2003

(65) Prior Publication Data

US 2004/0092949 A1 May 13, 2004

Related U.S. Application Data

(60) Provisional application No. 60/387,490, filed on Jun. 10, 2002.

(51) Int. Cl.
*A61B 17/58* (2006.01)

(52) U.S. Cl. .................................... 606/102

(58) Field of Classification Search ................ 606/86, 606/102
See application file for complete search history.

(56) References Cited

U.S. PATENT DOCUMENTS 5,700,268 A * 12/1997 Bertin ....................... 606/102
5,788,705 A * 8/1998 Huddleston et al. ........ 606/102

* cited by examiner

*Primary Examiner*—Eduardo C Robert
*Assistant Examiner*—Michael J. Araj
(74) *Attorney, Agent, or Firm*—Williams, Morgan & Amerson, P.C.

(57) ABSTRACT

A method and apparatus for performing minimally invasive hip replacement surgery using a T-handle ruler to make measurements inside the surgical site to assist in implanting a prosthetic femoral hip into the intramedullary canal of the natural femur. The ruler has an elongated central body and two measuring ends that are angled with respect to the central body.

23 Claims, 2 Drawing Sheets

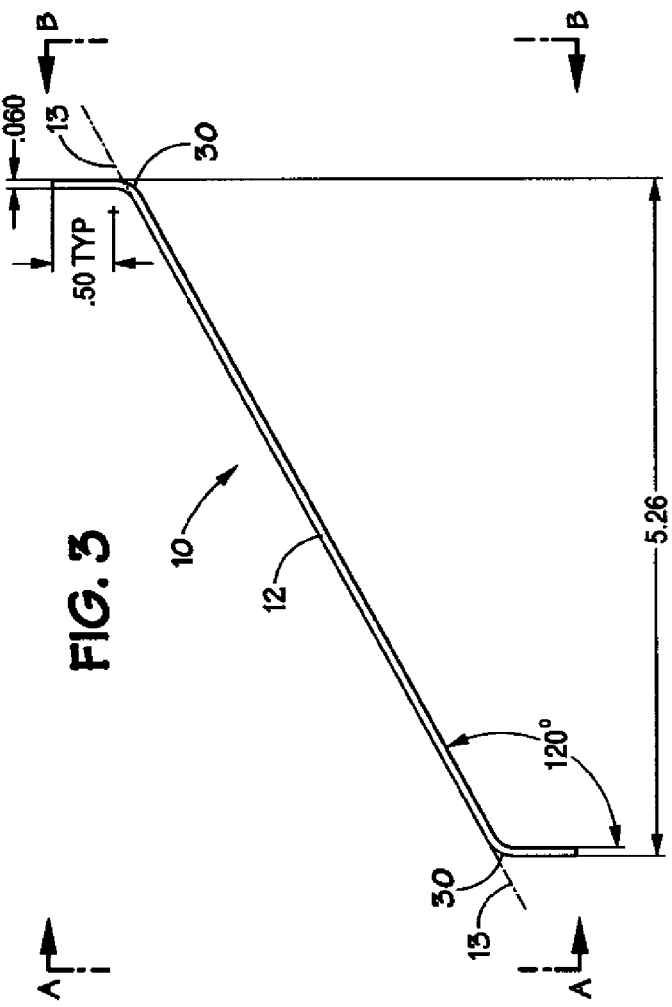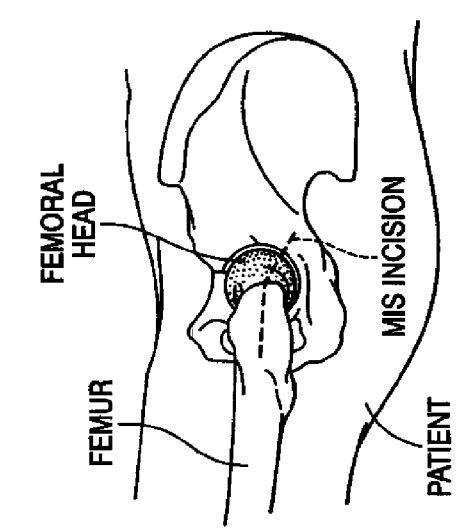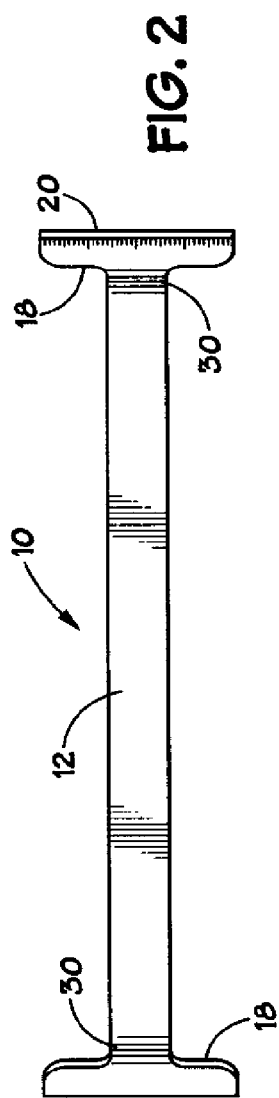
FIG. 1
FIG. 2
FIG. 3

METHOD OF USING T-HANDLE RULERS IN MINIMALLY INVASIVE HIP SURGERY

CROSS-REFERENCE TO RELATED APPLICATIONS

This application claims benefit of priority of U.S. Provisional Application Ser. No. 60/387,490 filed Jun. 10, 2002.

FIELD OF THE INVENTION

The disclosure herein generally relates to a method and apparatus for performing minimally invasive hip replacement surgery using T-handle rulers to make measurements inside the surgical site to assist in implanting a prosthetic femoral hip into the intramedullary canal of the natural femur.

BACKGROUND OF THE INVENTION

Traditional hip replacement surgery has been used in the United States since as early as the 1960's. The surgical technique to implant a hip has not drastically changed over the years, and today, this technique is quite successful. In fact, the surgical technique is prolifically used throughout the world and has a known success rate of over 90%. Certainly, the traditional surgical technique is fundamentally sound and predictable.

Unfortunately, traditional techniques to implant a hip have well recognized shortcomings. Most importantly, a rather large incision is made on the side of the hip. The incision can extend from 6 to 12 inches; the actual length of the incision depends on the size of the patient and type of surgery (revision versus total hip arthroplasty, for example). A long, deep incision can divide a number of important stabilizing muscles and tendons and further damage the hip joint and surrounding soft tissue. Inevitably, long incisions lead to larger blood losses, longer rehabilitation times for patients, and unsightly scar lines. A patient can easily spend four or five days in the hospital after a total hip arthroplasty, for example.

Recently, surgeons have been developing new, less invasive surgical techniques to perform total hip arthroplasty and revision hip surgery. Minimally invasive surgery, or MIS, is one such technique with great promise to become a popular and accepted technique for implanting a hip.

MIS has significant advantages over traditional hip replacement surgery. Most importantly, a rather small incision is made on the side on the hip. This incision is approximately 3 to 5 inches long, and the benefits of a shorter incision are enormous.

First and foremost, the patient can recover in a much shorter period of time after a MIS. The recuperation time in the hospital can be a few days and significantly reduce the cost to both the patient and hospital. In fact, some patients are leaving the hospital within 24 to 48 hours after the surgery. Obviously, this shortened time period is extremely important to the patient.

As another advantage, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Presently, instruments to perform MIS are being developed and refined. These instruments have a vital role in the ability to perform a successful minimally invasive surgery. These instruments, for example, must enable the surgeon to place the hip implant in a very precise location. If the implant is not accurately placed, then complications, such as dislocation or subluxation, can occur. Further and most importantly, the instruments must consistently and reliably perform through a small three inch opening in the patient.

A successful design of instruments for MIS has other challenges as well. Specifically, the instrument must be easy to use and facilitate the implantation procedure. If the MIS instrumentation is too cumbersome or not easy to manipulate, then the surgeon will be less likely to use minimally invasive surgery. The patient, then, will not reap the benefits MIS has to offer.

As yet another consideration, MIS instrumentation must appeal to a wide range of orthopedic surgeons with various skills and experience. If, for example, the instruments are too complex and complicated, then they will not be appealing and accepted in the orthopedic surgical community. Further yet, the training and skill level required to use the instruments and become proficient with them, cannot be overly taxing on the orthopedic surgeons.

While implanting or repairing a prosthetic femoral prosthesis in MIS for instance, measurements must be taken inside of the actual wound channel or surgical site. Accurate measurements are extremely important for properly sizing and fitting the femoral prosthesis into the intramedullary canal. During a traditional total hip arthroplasty or revision surgery, a ruler is used to make these measurements. These traditional rulers, though, are not shaped and sized to perform well in MIS. Specifically, the rulers are generally too long or too large to fit properly through the very small MIS incision. Additionally, the rulers are generally straight. If a straight ruler is positioned through an MIS incision, then the ruler itself or hand of the user can obstruct the line of site into the wound channel or surgical site. Further, it may be very difficult or even impossible to read the calibrated markings on the ruler since some measurements are taken at an angle inside the surgical site. Straight rulers simply will not work well in this situation.

A great advantage would be realized if a ruler were designed to make measurements inside the surgical site of MIS for hip replacement or reconstruction. Such a ruler would be shaped and sized to fit through the small MIS incision. Further, measurements could be taken without obstructing the line of sight into the surgical site. These measurements could be taken even if they were disposed at an angle in the surgical site. Other benefits as well would be realized from a ruler designed to be used with MIS.

In short, instruments, and in particular rulers for making measurements inside the surgical site, play a vital role in MIS surgery for hip implantation. It therefore would be advantageous to provide a new method and accompanying instrument for making measurements inside the surgical site in minimally invasive surgery.

SUMMARY OF THE INVENTION

The present invention is directed to a method and apparatus for performing minimally invasive hip replacement surgery using T-handle rulers to make measurements inside the surgical site to assist in implanting a prosthetic femoral hip into the intramedullary canal of the natural femur.

The method of the present invention generally comprises the steps of templating the side of the femur to be reconstructed; incising the surgical site with a minimally invasive incision from about 2½ inches to about 5 inches in length; providing retractors to retract soft tissue; dislocating the hip from the acetabulum; providing a T-handle ruler having an elongated straight central body and at least one T-shaped measuring end that is angled with respect to the central body; positioning the T-shaped measuring end through the incision and into the surgical site; measuring anatomical landmarks with the measuring end; transecting the femoral neck of the femur; reaming and broaching the intramedullary canal; placing a planar over a broach to plane the calcar; implanting a femoral prosthesis; providing a femoral head holder and impaction instrument; attaching a trial head to the femoral prosthesis using the instrument; removing the trial head from the prosthesis and from the instrument; attaching the final head to the instrument; inserting the final head and instrument into the surgical site; positioning the final head on the neck of the femoral prosthesis; impacting an end of the instrument to drive the final head onto the neck of the femoral prosthesis; detaching the instrument from the final head; removing all instruments from the surgical site; and closing the surgical site.

The instrument of the present invention is a T-handle ruler. This ruler generally comprises an elongated straight central body having two ends. A first measuring end is connected to one end of the body, and a second measuring end is connected to the other end of the body. Each measuring end forms a T-shape with the central body. Further, these measuring ends are angled with respect to the longitudinal axis of the body. Specifically, a smooth curved portion forms a transition between the central body and each T-shaped measuring end. Preferably, the measuring ends curve away from the body in opposite directions with respect to each other. As such, the body has a side view profile shaped as an "S" and a top view profile shaped as an "H."

One important advantage of the present invention is that the method and instrument are used in a minimally invasive orthopedic hip surgery. A single, small three to five inch incision is made at the surgical site on the side on the hip. The method of the present invention, thus, enjoys the benefits of a shorter incision compared to traditional hip surgery that uses a much longer incision. As one benefit, the patient can recover in a much shorter period of time after a MIS. The recuperation time in the hospital can be a few days and significantly reduce the cost to both the patient and hospital. This shortened time period is extremely important to the patient. Further, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Another important advantage of the present invention is that the T-handle ruler is specifically shaped and sized to be used in MIS. The measuring ends of the ruler have a T-shape that can easily fit through the small MIS incision and into the surgical site.

Another important advantage of the present invention is that the ruler has a measuring end that is angled with respect to the elongated central body. While the measuring end is positioned through the incision and inside the surgical site, the ruler will not obstruct the line of site into the wound channel. Further, the calibrated markings on the measuring end can be easily read even while the ruler is positioned in the surgical site.

Further yet, the instrument is easy to use and facilitates the implantation procedure. The ruler is sized and shaped to fit through the MIS incision and has calibrated markings that are easily read while in the surgical site. As such, use of the ruler can appeal to a wide range of orthopedic surgeons with various skills and experience. Further yet, the training and skill level required to use the ruler and become proficient with it is not overly taxing on the orthopedic surgeon.

BRIEF DESCRIPTION OF THE DRAWINGS

FIG. 1 is a sketch of a patient showing a femur and femoral head positioned in the acetabulum with an MIS incision marked along the hip.

FIG. 2 is a top perspective view of the T-handle ruler of the present invention.

FIG. 3 is a side view of the T-handle ruler showing dimensional measurements.

DETAILED DESCRIPTION

Figure 4:
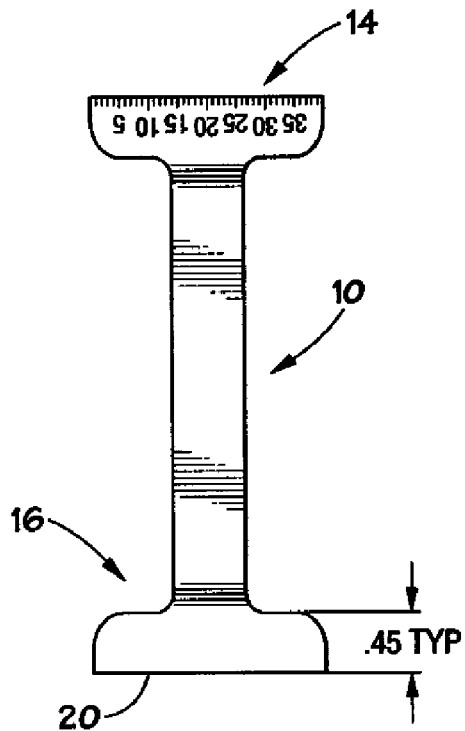
FIG. 4 is a view taken along the lines A—A of FIG. 3 showing dimensional measurements.
Figure 5:
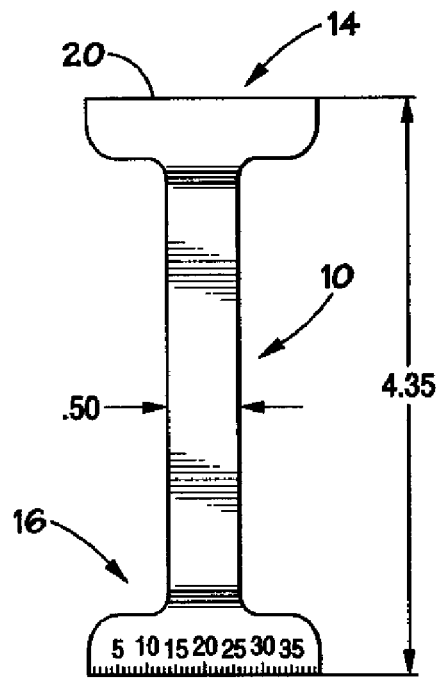
FIG. 5 is a view taken along the lines B—B of FIG. 3 showing dimensional measurements.

The instruments, method, and steps of the present invention are now described in more detail. The method describes the steps to perform a minimally invasive surgery to implant a prosthetic femoral hip stem in the intramedullary canal of a natural femur. Some of these steps described in the method are known to those skilled in the art and will not be discussed in great detail. Further, one skilled in the art will appreciate that certain steps may be altered or omitted while other steps may be added without departing from the scope of the invention. The novel steps of the present invention, for example, can be applied to total hip arthroplasty, to revision surgeries for total and partial hip replacement, and to other orthopedic hip surgeries using minimally invasive surgical techniques.

To facilitate a discussion of the present invention, the method of implanting a prosthetic femoral hip stem is divided into a plurality of steps or sections. Each of these sections is discussed seriatim.

More specifically, the method of the present invention teaches how to use a T-handle ruler to make measurements inside the surgical site to assist in implanting a prosthetic femoral hip into the intramedullary canal of the natural femur. For illustrative purposes, the discussion focuses on implanting a Natural™ Hip System of Centerpulse Orthopedics Inc. of Austin, Tex. This system illustrates one possible hip system that can be used. One skilled in the art will appreciate that other, different hip systems can also be used with the method and apparatus of the present invention without departing from the scope of the invention.

Templating the Femur

Typically, the side of the femur to be reconstructed is templated. Use of a template enables the surgeon to make an estimation of the size of instruments, trials, and prosthetic components to be used during the surgical procedure. Templating and other preoperative techniques will also help to identify bone abnormalities and other potential problems before the surgery. Further, these procedures aid the surgeon in restoring the center of rotation of the hip and placing the femoral prosthesis with the correct length and offset. The exact procedures for templating the femur are known in the art and will not be discussed in detail Incising the Surgical Site (See FIG. 1)

A relatively small, single minimally invasive incision is made at the surgical site. A minimally invasive incision for this procedure has a length from about 2½ inches to about 4 or 5 inches. The incision is slightly curved or straight, commences near the vastus tubercle, and continues toward the greater trochanter and posterior inferior spine. The incision should be carried down through subcutaneous tissue and fascia lata. Any muscle tissue should be gently split in line with its fibers. At this time, a leg length measurement can be taken using techniques known in the art.

Providing Retractors

The retractors have an elongated, flat, thin body with two primary sections, a handle section and a retracting section. The handle section is elongated and adapted to be gripped with a hand. A smooth curved section transitions the handle section to the retracting section. The retracting section typically has a paddle and may further include a prong.

Dislocating the Hip from the Acetabulum

Next, dislocation of the hip occurs. A bone hook or skid may be used to avoid excess torsion on the femoral shaft.

Providing T-Handle Ruler (See FIGS. 2–5)

The ruler generally comprises an elongated straight central body having two ends. A first measuring end is connected to one end of the body, and a second measuring end is connected to the other end of the body. Each measuring end forms a T-shape with the central body. Further, these measuring ends are angled with respect to the longitudinal axis of the body. Specifically, a smooth curved portion forms a transition between the central body and each T-shaped measuring end. Preferably, the measuring ends curve away from the body in opposite directions with respect to each other. As such, the body has a side view profile shaped as an "S" and a top view profile shaped as an "H." The ruler is described in more detail with reference to the figures.

Figure 6:
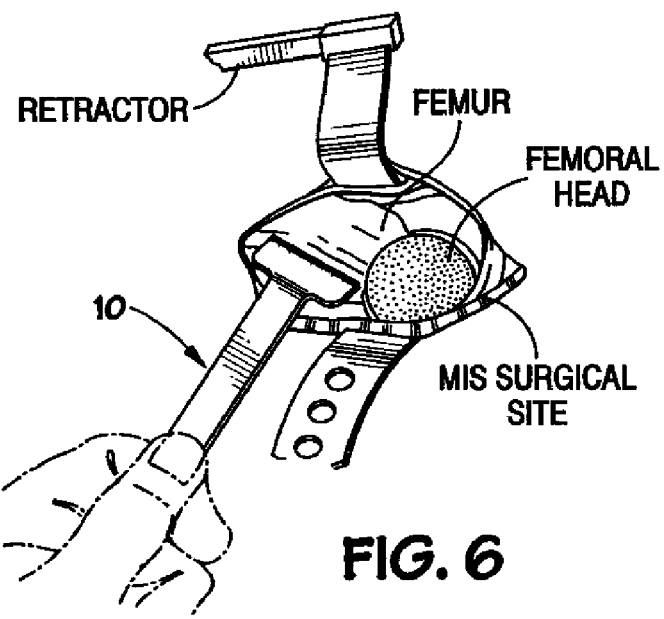
FIG. 6 is a sketch of the T-handle ruler positioned through an MIS surgical incision to take measurements of the natural femur.

Positioning the Ruler Through the Incision and into the Surgical Site (See FIG. 6)

The measuring end of the ruler is shaped and sized so it can be positioned through the incision and into the surgical site. Preferably, these ends have a length between about 15 mm to about 7 cm. If the length of the end of the ruler is longer than the incision, then the tip of either T-shaped end can be positioned through the incision and then the ruler rotated. In this manner, the length of the incision can actually be less than the length of the T-shaped measuring end.

Taking Measurement Inside the Surgical Site (See FIG. 6)

Once the measuring end is positioned into the surgical site, various measurements can be taken to assist the surgeon in properly placing and fitting the femoral prosthesis into the intramedullary canal of the patient. For example, a measurement can first be made on the bony femoral anatomy of the patient. Generally, this measurement is made from the eminence of the lesser trochanter to the predetermined calcar resection level. Sometimes, a measurement from the planned calcar resection level to the femoral head center is also made. Other measurements to various landmarks that the surgeon deems important can also be made at any time during the surgical procedure. Once the measurements are made, the ruler is removed from the surgical site.

Transecting the Femoral Neck

Retractors may be placed at various locations, for example under the femoral head or lesser trochanter, in order to achieve better visualization for proper transection of the femoral neck at the templated level. Measurements taken with the ruler can aid the surgeon in determining the proper transection location. Care should be taken to protect the sciatic nerve.

Preparing the Intramedullary Canal

After completing preparation of the acetabulum, the femur may be rotated for a better position, and retractors may be used to lift the femur and retract posterior soft tissue.

Proportional sized tapered reamers with blunt tips are used to prepare the intramedullary canal. The reamers have a calcar stop to assure proper depth of penetration. Generally, reaming occurs laterally against the greater trochanter to ensure that the reamer enters the canal in a neutral position. Each reamer can be followed with a correspondingly sized broach. The broach has cutting teeth to help prepare the canal. This sequence of reaming and broaching continues until the next to the last templated size broach is inserted. This next to last broach is used for the calcar planing process.

A calcar planar is placed over the proximal broach, and the calcar is planed flat to allow proper seating of the collar on the stem. Measurements taken with the ruler can aid the surgeon in determining the proper end point for calcar planing. Once calcar planing is finished, the final reamer and broach sequence is performed. The final broach should fill the proximal region and be stable. The final broach can be used to trial the appropriate head/neck adaptor.

Implanting the Femoral Prosthesis

Proper size of the femoral prosthesis is based on the size of the final broach. Once an implant is selected, it is attached to a femoral implant holder. The holder assists in controlling rotation and enables the implant to be inserted into the intramedullary canal with proper anteversion. A mallet or slaphammer can be used to impact the implant and fully seat it to a final position with the collar contacting the calcar.

Providing a Femoral Head Holder and Impaction Instrument

A femoral head holder and impaction instrument is provided. This instrument includes two major components, a driver and a holder. The driver has a handle and a shaft that extends outwardly from the handle. A distal end of the shaft includes external threads. The holder has a body with a conical shape that forms an internal socket adapted to receive and hold a femoral head. A proximal end of the body includes a threaded bore adapted to receive the external threads on the driver. The body further includes a plurality of flexible fingers that extend outwardly to form the socket. A relief cut is formed in the body where several fingers have been removed.

Attaching a Trial Head to the Femoral Prosthesis

A trial head is provided and attached the holder of the instrument. Specifically, the head is snapped into the socket of the holder with the open face of the trial head facing backwards and out through the relief cut. The holder is threadably connected to the driver, if this step has not yet been completed.

Next, the trial head and holder are positioned through the surgical site until the opening of the trial head aligns with the neck of the femoral prosthesis. The handle of the instrument is then pulled downwardly or toward the distal portion of the femoral prosthesis so the trial head seats or engages on the trunion taper of the neck. Continue pulling until the holder snaps off of the trial head.

Removing a Trial Head from the Femoral Prosthesis

In order to remove a trial head from the femoral prosthesis, position the socket of the holder approximately perpendicular to or superior to the neck. Push the holder onto the trial head so the socket snaps over the trial head. Next, rotate the instrument toward the distal end of the femoral prosthesis so the relief cut is adjacent the neck. In this position, the trial head is captured inside the holder. Push the instrument upwardly toward the proximal end of the femoral prosthesis in a direction generally parallel with the stem. The trial head should pull off from the stem and be captured in the socket of the holder. Remove the holder and trial stem from the surgical site.

Attaching a Final Head to the Femoral Prosthesis

A final head is provided and attached the holder of the instrument. Specifically, the head is snapped into the socket of the holder with the open face of the head facing backwards and out through the relief cut. The holder is threadably connected to the driver, if this step has not yet been completed.

Next, the final head and holder are positioned through the surgical site until the opening of the head aligns with the neck of the femoral prosthesis. The handle of the instrument is then pulled downwardly or toward the distal portion of the femoral prosthesis so the head seats or engages on the trunion taper of the neck.

While the head is still engaged in the socket of the holder, rotate the instrument upwardly toward the final head so the instrument is generally parallel with the axis of the stem. Provide a mallet or similar device and impact the proximal end of the instrument adjacent the handle. Continue to impact the instrument until the head is fully seated on the neck of the femoral prosthesis.

Once the head is fully seated and while the instrument is still generally parallel with the axis of the stem, pull the handle of the instrument away from the head until the socket snaps out of engagement with the head. The snap serves as an audible verification that the head is fully seated on the neck. Remove the holder from the surgical site.

Closing Surgical Site

Once the femoral head is firmly connected to the prosthetic femur, all instruments and devices are removed from the site. The prosthetic femur and femoral head should now be properly positioned. A final inspection of the joint should be made to ensure no residual material or osteophytes are present.

Closure of the site may occur with well known techniques. Further, this disclosure will not discuss post-operative protocol or rehabilitation as such procedures are known in the art and tailored to meet the specific needs of the patient.

Detailed Description of the T-Handle Ruler

One important advantage of the present invention is that the T-handle ruler is specifically designed and adapted to be used in minimally invasive surgical techniques for making measurements while the measuring end is positioned through the small MIS incision. These measurements aid the surgeon in determining proper implantation of the femoral prosthesis into the intramedullary canal of a patient.

FIGS. 2–5 show the T-handle ruler 10 of the present invention. This ruler generally comprises an elongated straight central body 12 having two measuring ends. The body has a thin, flat rectangular shape with a longitudinal axis 13 (FIG. 3) that extends through the center as shown.

A first measuring end 14 is connected to one end of the body, and a second measuring end 16 is connected to the other end of the body. Each measuring end forms a T-shape with the central body 12. The measuring ends are configured to have a somewhat elongated rectangular shape or dome-shape, having one side of the rectangular shape with a rounded edge 18. One side of each end has a straight edge 20. These edges are calibrated with permanent measuring markings engraved into measuring ends themselves. These markings can be calibrated to show millimeters, centimeters, inches, or the like. As a further advantage, the markings can be switched at each end to provide both left and right reading. Specifically, on one end of the measuring end, the markings can commence with zero and progress toward higher scale readings from a left to right orientation. On the other end of the measuring end, the markings can commence with zero and progress toward higher scale readings from a right to left orientation.

The straight edges 20 can have various lengths. This length, though, should be commensurate for use in MIS as described herein. Lengths of 7 cm and 15 mm can be provided, for example.

One critical feature of the present invention is that the measuring ends are angled or bent with respect to the longitudinal axis of the body. Specifically, a smooth curved portion 30 forms a transition between the central body 12 and each T-shaped measuring end. Preferably, the measuring ends curve away from the body in opposite directions with respect to each other. As such, the body has a side view profile shaped as an "S" and a top view profile shaped as an "H."

The angulation of the measuring ends provides numerous advantages. While the measuring end is positioned through the incision and inside the surgical site, the ruler will not obstruct the line of site into the wound channel. Further, the calibrated markings on the measuring end can be easily read even while the ruler is positioned in the surgical site. Further the angled measuring end can be flush with the bone being measured and yet easily read from outside the surgical site. Thus, the scale markings themselves are more visible when viewed from outside the surgical site because the measuring ends are angled.

In the preferred embodiment, each measuring end has a T-shape. As alternate embodiment, the ruler could be provided with only one T-shaped measuring end. The other end could be shaped as a handle and adapted to be gripped in a hand.

In the preferred embodiment, the measuring ends each have a T-shape with the same size. As an alternate embodiment, the measuring ends could be provided with different sizes from each other. A surgeon could, thus, choose between one of two sized ends to insert into the surgical incision depending on what measurement needed to be taken. Further, the measuring ends could be calibrated differently. For example, one end could be calibrated or scaled in millimeters while the other end was calibrated in centimeters. Various combinations with different calibrations and sized ends are within the scope of the invention.

It should be emphasized that although the method of the present invention was described with a specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention. Further, although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for making measurements inside a minimally invasive surgical site to implant a prosthetic femur into an intramedullary canal of a patient, comprising the steps of:
   incising a hip and creating a surgical site with a minimally invasive incision with a length of about 2½ inches to about 4 to 5 inches to access a natural femur of the patient;
   providing a ruler having an elongated central body with two measuring ends disposed at opposite ends of the body, each of the measuring ends having a T-shape and being angled with respect to the body, each of said measuring ends comprising measuring markings;
   positioning one of the measuring ends of the ruler through the incision and into the surgical site;
   taking measurements with the measuring end while positioned in the surgical site;
   removing the ruler from the surgical site;
   transecting a femoral head of a natural femur;
   implanting the prosthetic femur into the intramedullary canal; and
   closing the incision.

2. The method of claim 1 further comprising the step of providing at least one of the measuring ends to have an elongated dome-shape.

3. The method of claim 1 further comprising the step of providing the ruler to have an S-shape in a side profile view.

4. The method of claim 3 further comprising the step of providing the ruler to have an H-shape in a top profile view.

5. The method of claim 1 further comprising the step of providing the body with a smooth curved portion that transitions between the body and the measuring end.

6. A method for using a ruler inside a minimally invasive surgical site to implant a prosthetic femur into an intramedullary canal of a patient, comprising the steps of:
   incising a hip and creating a surgical site with a minimally invasive incision with a length of about 2½ inches to about 5 inches;
   providing a ruler having an elongated central body with two measuring ends and with a longitudinal axis extending through the body, each measuring end has a T-shape and is angled with respect to the body;
   positioning one of the measuring ends of the ruler through the incision and into the surgical site;
   taking measurements with the measuring end while positioned in the surgical site;
   removing the ruler from the surgical site;
   implanting the prosthetic femur into the intramedullary canal; and
   closing the incision.

7. The method of claim 6 wherein the step of providing the measuring ends with the angle being with respect to the longitudinal axis.

8. The method of claim 7 further comprising the step of providing a smooth curved portion between each measuring end and the central body to provide the angle.

9. The method of claim 8 further comprising the step of providing the measuring ends to angle away from the body in opposite directions with respect to each other.

10. The method of claim 6 further comprising the step of providing the ruler with an S-shape profile.

11. The method of claim 10 further comprising the step of providing the ruler with an H-shape profile.

12. The method of claim 6, further comprising providing measuring markings on at least one of said two measuring ends.

13. The method of claim 6, further comprising providing measuring markings on each of said two measuring ends.

14. A method of taking measurements inside a minimally invasive surgical site to implant a prosthetic femur into an intramedullary canal of a patient, comprising the steps of:
   incising a hip and creating a surgical site with a minimally invasive incision with a length of about 2½ inches to about 5 inches;
   providing a ruler having an elongated central body with two measuring ends, each measuring end has a T-shape and is angled with respect to the body;
   positioning one of the measuring ends through the incision and into the surgical site;
   taking measurements with the measuring end while the measuring end is positioned in the surgical site;
   removing the ruler from the surgical site;
   implanting the prosthetic femur into the intramedullary canal; and
   closing the incision.

15. The method of claim 14 further comprising the step of providing the ruler with two smooth curved portions, each curved portion connects one end of the central body to one of the measuring ends.

16. The method of claim 15 further comprising the step of providing the rule with an S-shape.

17. The method of claim 16 further comprising the step of providing the ruler with an H-shape.

18. The method of claim 17 further comprising the step of providing the measuring ends with a straight, tapering edge.

19. The method of claim 14 further comprising the step of providing the measuring end with a length of between about 15 mm to 7 cm.

20. The method of claim 14, further comprising providing measuring markings on at least one of said two measuring ends.

21. The method of claim 14, further comprising providing measuring markings on each of said two measuring ends.

22. A method for making measurements inside a minimally invasive surgical site to implant a prosthetic femur into an intramedullary canal of a patient, comprising the steps of:
   incising a hip and creating a surgical site with a minimally invasive incision to access a natural femur of the patient;
   providing a ruler having an elongated central body with at least one measuring end disposed at an end of the body, said ruler having an S-shape in a side profile view and said measuring end having a T-shape and being angled with respect to the body;

positioning the measuring end of the rule through the incision and into the surgical site;

taking measurements with the measuring end while positioned in the surgical site;

removing the ruler from the surgical site;

transecting a femoral head of a natural femur;

implanting the prosthetic femur into the intramedullary canal; and closing the incision.

23. A method for making measurements inside a minimally invasive surgical site to implant a prosthetic femur into an intramedullary canal of a patient, comprising the steps of:

incising a hip and creating a surgical site with a minimally invasive incision to access a natural femur of the patient;

providing a ruler having an elongated central body with at least one measuring end disposed at an end of the body, the measuring end having a T-shape and being angled with respect to the body, said body having a smooth curved portion that transitions between the body and the measuring end;

positioning the measuring end of the rule through the incision and into the surgical site;

taking measurements with the measuring end while positioned in the surgical site;

removing the ruler from the surgical site;

transecting a femoral head of a natural femur;

implanting the prosthetic femur into the intramedullary canal; and closing the incision.

* * * * *